United States Patent
Aljar

(10) Patent No.: US 11,859,991 B2
(45) Date of Patent: Jan. 2, 2024

(54) METHOD, APPARATUS, AND SYSTEM FOR IDENTIFYING ONE OR MORE SOURCES OF AIR POLLUTANTS BASED ON EMISSION DATA FROM VEHICLES AND AIR QUALITY DATA FROM AMBIENT AIR MEASUREMENT APPARATUSES

(71) Applicant: Saudi Arabian Oil Company, Dhahran (SA)

(72) Inventor: Faisal S. Aljar, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 162 days.

(21) Appl. No.: 17/687,818

(22) Filed: Mar. 7, 2022

(65) Prior Publication Data
US 2023/0280173 A1    Sep. 7, 2023

(51) Int. Cl.
*G01C 21/34*    (2006.01)
*B60W 50/12*    (2012.01)
(Continued)

(52) U.S. Cl.
CPC ......... *G01C 21/3469* (2013.01); *B60W 20/16* (2016.01); *B60W 50/12* (2013.01);
(Continued)

(58) Field of Classification Search
None
See application file for complete search history.

(56) References Cited

U.S. PATENT DOCUMENTS 8,509,991 B2 * 8/2013 Bai .................... B60H 1/00771
701/36
8,903,646 B2 * 12/2014 Althen .................. G06Q 99/00
701/411

(Continued)

FOREIGN PATENT DOCUMENTS

CN    105868568 A * 8/2016    ......... G01N 33/0004
CN    110386132 A * 10/2019    ............ B60W 20/16
(Continued)

OTHER PUBLICATIONS

Rathod et al. "An air pollutant vehicle tracker system using gas sensor and GPS." 2017 International conference of Electronics, Communication and Aerospace Technology (ICECA). vol. 1. IEEE, 2017. pp. 494-498.

(Continued)

*Primary Examiner* — Kevin R Steckbauer
(74) *Attorney, Agent, or Firm* — Leason Ellis LLP

(57) ABSTRACT

An apparatus and a method for identifying one or more sources of an airborne pollutant in a geographical area and for mitigating release of the airborne pollutant, comprising: receiving emission data and vehicle location data associated with a plurality of corresponding vehicles in the geographical area; receiving ambient air quality data for respective locations in the geographical area; apply a vehicle emission plume air dispersion model to process the received emission data, the received vehicle location data, and the received ambient air quality data; identify one or more principal sources of the airborne pollutant based on the processed emission data, vehicle location data, and ambient air quality data; and transmit an instruction related to one or more vehicles associated with the one or more identified principal sources of the airborne pollutant.

18 Claims, 5 Drawing Sheets

(51) Int. Cl.
- G01N 33/00 (2006.01)
- B60W 20/16 (2016.01)
- *G06F 17/10* (2006.01)
- *G16Y 20/10* (2020.01)
- *G16Y 40/10* (2020.01)
- *G01N 1/02* (2006.01)

(52) U.S. Cl.
CPC . *G01N 33/0004* (2013.01); *B60W 2554/4041* (2020.02); *B60W 2555/20* (2020.02); *G01N 2001/021* (2013.01); *G06F 17/10* (2013.01); *G16Y 20/10* (2020.01); *G16Y 40/10* (2020.01); *Y02A 50/20* (2018.01)

(56) References Cited

U.S. PATENT DOCUMENTS

| | | | | |
|---|---|---|---|---|
| 9,719,972 | B2* | 8/2017 | Cogill | G01S 19/14 |
| 9,952,190 | B2* | 4/2018 | Cogill | G01N 1/2273 |
| 10,272,909 | B1* | 4/2019 | Melatti | B60W 20/40 |
| 10,887,722 | B2* | 1/2021 | Borrel | H04L 67/52 |
| 10,890,350 | B2* | 1/2021 | Martin | G01N 33/0075 |
| 11,226,323 | B2* | 1/2022 | Ba | G01N 33/0075 |
| 2004/0039517 | A1* | 2/2004 | Biesinger | G08G 1/01 340/907 |
| 2015/0077737 | A1* | 3/2015 | Belinsky | G01N 15/0211 250/208.2 |
| 2016/0290977 | A1* | 10/2016 | Cogill | G01N 33/004 |
| 2016/0290979 | A1* | 10/2016 | Cogill | G01N 33/004 |
| 2020/0064318 | A1* | 2/2020 | Keni | G01N 33/0004 |
| 2023/0280173 | A1* | 9/2023 | Aljar | B60W 50/12 701/123 |

FOREIGN PATENT DOCUMENTS

| | | | | |
|---|---|---|---|---|
| CN | 110472850 | A * | 11/2019 | |
| CN | 111175441 | A * | 5/2020 | ......... G01N 33/0004 |
| CN | 212568705 | U * | 2/2021 | |
| CN | 113156060 | A * | 7/2021 | |
| CN | 113375723 | A * | 9/2021 | |
| CN | 110189026 | B * | 11/2021 | .......... G06N 3/0445 |
| CN | 113610384 | A * | 11/2021 | |
| CN | 113624921 | A * | 11/2021 | |
| CN | 215180012 | U * | 12/2021 | |
| CN | 114217014 | A * | 3/2022 | |
| CN | 114522262 | A * | 5/2022 | |
| CN | 114693003 | A * | 7/2022 | |
| CN | 114734771 | A * | 7/2022 | |
| CN | 114755367 | A * | 7/2022 | |
| CN | 114880626 | A * | 8/2022 | |
| CN | 114693003 | B * | 9/2022 | |
| CN | 115327038 | A * | 11/2022 | |
| CN | 116029411 | A * | 4/2023 | |
| CN | 116070839 | A * | 5/2023 | |
| CN | 116090673 | A * | 5/2023 | |
| DE | 10043797 | A1 | 3/2002 | |
| DE | 202015007355 | U1 | 1/2016 | |
| DE | 102019109945 | A1 * | 10/2019 | ............ B60W 20/16 |
| DE | 102021130004 | A1 * | 5/2022 | |
| DE | 102021132588 | A1 * | 12/2022 | |
| DE | 102021132591 | A1 * | 12/2022 | |
| TW | 202016750 | A * | 5/2020 | |

OTHER PUBLICATIONS

Wang et al. "A Real-Time Vehicle Exhaust Gas Monitoring Enabled Optimization Approach for Air Pollution Control." Applied Mechanics and Materials, vol. 602-605, Trans Tech Publications, Ltd., Aug. 2014, pp. 2011-2014. doi:10.4028/www.scientific.net/amm.602-605.2011.

* cited by examiner

METHOD, APPARATUS, AND SYSTEM FOR IDENTIFYING ONE OR MORE SOURCES OF AIR POLLUTANTS BASED ON EMISSION DATA FROM VEHICLES AND AIR QUALITY DATA FROM AMBIENT AIR MEASUREMENT APPARATUSES

FIELD OF THE DISCLOSURE

The present disclosure generally relates to environmental monitoring systems.

BACKGROUND OF THE DISCLOSURE

With the continued proliferation of automobiles, many cities are facing high ambient air pollution concentrations due to high traffic volumes. Additionally, aging vehicles and lack of maintenance can further contribute to the pollution. Consequently, air pollution during rush hours or other peak traffic periods can reach dangerous pollution levels, which can cause public health issues. Vehicle maintenance programs can improve the emissions of some vehicles but is insufficient in addressing all problematic vehicles, especially those belonging to noncompliant individuals.

SUMMARY OF THE DISCLOSURE

In view of the above, the present disclosure provides an improved technique for monitoring the air quality in geographical regions, especially urban areas. The improved technique of the present disclosure combines several concepts, including without limitation, air pollution monitoring, air dispersion modeling, vehicle GPS, and vehicle emissions exhaust monitoring for monitoring the overall ambient air quality of an area and, more specifically, identifying and locating mobile sources of air pollution. In other words, real-time air pollution levels and contributions from each vehicle is determined.

According to one or more example implementations, ambient air monitoring used to measure an air quality index in a geographical area is augmented with individual vehicle emission monitoring to provide more robust and detailed measurements on traffic pollution. As a result, more immediate and direct actions, such as diverting traffic, to avoid reaching dangerous air pollution levels are provided for by the present disclosure. Additionally, any noncompliant vehicles to emission standards are quickly and accurately identified for remedial actions.

In accordance with one or more example implementations, the present disclosure provides for determining the effects of introducing of new transportation fuels and technologies and the efficacy of vehicle maintenance mandates on emissions. The present disclosure further provides modelling that is relevant to public health epidemiology, that improves upon mobile emission sources dispersion models, determining ambient dispersion of pollutants, and the accuracy of issuing citations to pollutions sources (mobile sources or nearby stationary sources).

According to an example implementation of the present disclosure, an apparatus adapted to identify one or more sources of an airborne pollutant in a geographical area and to mitigate release of the airborne pollutant, comprises: a processor; a communication interface to one or more networks; a non-transitory computer-readable memory operatively connected to the processor and having stored thereon machine-readable instructions to: receive, via the communication interface from a plurality of emission data collection assemblies, emission data and vehicle location data associated with a plurality of corresponding vehicles in the geographical area; receive, via the communication interface from a plurality of ambient air quality collection assemblies at respective locations in the geographical area, ambient air quality data for the respective locations in the geographical area; apply a vehicle emission plume air dispersion model to process the received emission data, the received vehicle location data, and the received ambient air quality data; identify one or more principal sources of the airborne pollutant based on the processed emission data, vehicle location data, and ambient air quality data; and transmit, via the communication interface, an instruction related to one or more vehicles associated with the one or more identified principal sources of the airborne pollutant.

In an example implementation, the instruction comprises one or more of a distance limit and a time limit from a corresponding one or more of a location and a time associated with the identification of one or more principal sources of the airborne pollutant to render inoperable the one or more vehicles.

According to an example implementation, the instruction comprises a citation related to each of the one or more vehicles based on the identification of the one or more principal sources of the airborne pollutant.

In an example implementation, the instruction comprises an alert for performing maintenance services on the one or more vehicles based on the identification of the one or more principal sources of the airborne pollutant.

In an example implementation, the identification of the one or more principal sources of the airborne pollutant comprises identifying at least one vehicle without an emission data collection assembly as at least one of the one or more principal sources of the airborne pollutant.

In an example implementation, the at least one vehicle without an emission data collection assembly is identified based on the processed emission data and vehicle location data associated with one or more of the plurality of corresponding vehicles in a vicinity of the identified at least one vehicle.

In an example implementation, the at least one vehicle without an emission data collection assembly is identified based on the processed ambient air quality data for one or more of the respective locations in a vicinity of the identified at least one vehicle.

In an example implementation, the instruction comprises an alteration to an assigned route related to the one or more vehicles associated with the one or more identified principal sources of the airborne pollutant.

In an example implementation, the instruction comprises an alteration to one or more of a traffic light and a road sign related to the one or more vehicles associated with the one or more identified principal sources of the airborne pollutant.

According to an example implementation of the present disclosure, a method for identifying one or more sources of an airborne pollutant in a geographical area and for mitigating release of the airborne pollutant, comprises: receiving, by a processing apparatus via a communication interface from a plurality of emission data collection assemblies, emission data and vehicle location data associated with a plurality of corresponding vehicles in the geographical area; receiving, by the processing apparatus via the communication interface from a plurality of ambient air quality collection assemblies at respective locations in the geographical area, ambient air quality data for the respective locations in the geographical area; applying, by the processing apparatus, a vehicle emission plume air dispersion model to process the received emission data, the received vehicle location data, and the received ambient air quality data; identifying, by the processing apparatus, one or more principal sources of the airborne pollutant based on the processed emission data, vehicle location data, and ambient air quality data; and transmitting, by the processing apparatus via the communication interface, an instruction related to one or more vehicles associated with the one or more identified principal sources of the airborne pollutant.

In an example implementation, the instruction comprises one or more of a distance limit and a time limit from a corresponding one or more of a location and a time associated with the identifying of the one or more principal sources of the airborne pollutant to render inoperable the one or more vehicles.

In an example implementation, the instruction comprises a citation related to each of the one or more vehicles based on the identifying of the one or more principal sources of the airborne pollutant.

In an example implementation, the instruction comprises an alert for performing maintenance services on the one or more vehicles based on the identifying of the one or more principal sources of the airborne pollutant.

In an example implementation, the identifying of the one or more principal sources of the airborne pollutant comprises identifying at least one vehicle without an emission data collection assembly as at least one of the one or more principal sources of the airborne pollutant.

In an example implementation, the at least one vehicle without an emission data collection assembly is identified based on the processed emission data and vehicle location data associated with one or more of the plurality of corresponding vehicles in a vicinity of the identified at least one vehicle, In an example implementation, the at least one vehicle without an emission data collection assembly is identified based on the processed ambient air quality data for one or more of the respective locations in a vicinity of the identified at least one vehicle.

In an example implementation, the instruction comprises an alteration to an assigned route related to the one or more vehicles associated with the one or more identified principal sources of the airborne pollutant.

In an example implementation, the instruction comprises an alteration to one or more of a traffic light and a road sign related to the one or more vehicles associated with the one or more identified principal sources of the airborne pollutant.

BRIEF DESCRIPTION OF THE DRAWINGS

Various example implementations of this disclosure will be described in detail, with reference to the following figures, wherein.

DETAILED DESCRIPTION

Figure 1:
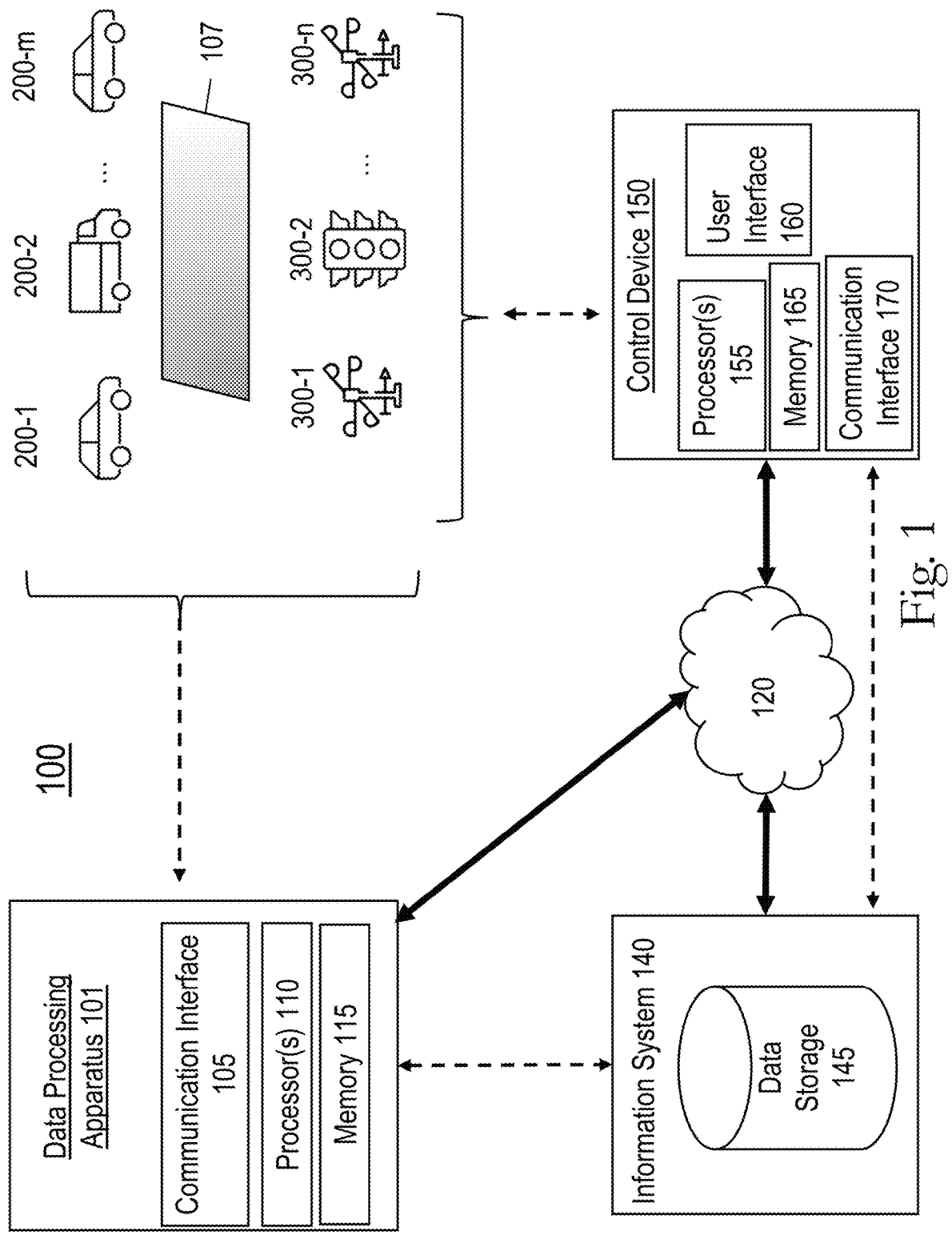
FIG. 1 is a schematic illustration of an air quality and emission data retrieval, processing, storage, and application system according to an example implementation of the present disclosure.

The headings used herein are for organizational purposes only and are not meant to be used to limit the scope of the description or the claims. As used throughout this application, the words "may" and "can" are used in a permissive sense (i.e., meaning having the potential to), rather than the mandatory sense (i.e., meaning must). Similarly, the words "include," "including," and "includes" mean including but not limited to. To facilitate understanding, like reference numerals have been used, where possible, to designate like elements common to the figures.

As discussed above, urban areas with high vehicular traffic volumes and/or concentrations suffer particularly high air pollution, especially during peak traffic periods, such as rush hours. In view of this growing issue as more automobiles continue to proliferate, there is an unmet need for monitoring large numbers of vehicles to maintain reasonable traffic concentrations and to ensure compliance with emission standards. The present disclosure provides for the real time accurate monitoring of large numbers of vehicles as well as overall air quality measures for an area associated with the vehicles to thereby provide immediately actionable information on improving the air quality for the area.

Among other features, the present disclosure provides for tracking service life, maintenance, and emission compliance of monitored vehicles. Additionally, the present disclosure provides for more accurate determination of noncompliant vehicles that may or may not be monitored based on data collected from monitored vehicles. In one or more example implementations, information on individual vehicles from onboard sensors is linked to ambient air quality measures from weather stations to more accurately determine the actual contributions of vehicles on the road to the air pollution (e.g., airborne pollutants and concentrations) in the area. More specifically, dispersion modeling is used among vehicle locations/emissions and station locations to accurately determine mobile sources of pollution (e.g., airborne pollutants and concentrations), including monitored and unmonitored vehicles, and their effects on ambient air pollution.

The present disclosure enhances vehicle mounted real-time emission sensors by augmenting the information provided by such sensors with station-based air quality measurements and with dispersion modeling algorithms for mobile emission sources. Additionally, the accuracy of vehicle location systems—such as, onboard global positioning systems (GPS), radio triangulation systems, and the like—is enhanced by the above-described combination of emission monitoring systems, where feedback processing of the emission data provides updated location information for the vehicles associated with the emission data. Furthermore, in one or more example implementations, a linkage between vehicular emission sensors, GPS, and vehicle information (such as fuel, engine, and maintenance data) is provided to more accurately determine factors related to the monitored vehicles that contribute to ambient air pollution, such as fuel types, engine types, engine age, service history, operating durations, to name a few.

Additionally, the present disclosure provides for a model that identifies the effects of each vehicle or fleet on ambient air quality, which aids regulators and policymakers on defining localized operating policies that best address traffic related air pollution.

Thus, advantageously, the present disclosure provides a technique for analyzing combined granular emission data with overall air quality data to customize remedial interventions that maximize the remedial effect of such interventions, which thereby reduces the frequency and any adverse impact of such interventions. For example, by timely and accurately identifying specific noncompliant vehicles, the present disclosure reduces the need for sweeping inspections on emission standard compliance and can target the specific vehicles to mitigate release of the air pollution (e.g., airborne pollutants).

FIG. 1 is a schematic illustration of an air quality and emission data retrieval, processing, storage, and application system 100 according to an example implementation of the present disclosure. It should be understood by one or ordinary skill in the art that one or more of the devices, apparatuses, and systems shown in FIG. 1, and as described below, can be divided into plural entities. Conversely, the features and functionality provided by any plural entities shown in FIG. 1, and as described below, can be provided by a consolidated apparatus with suitable programming and attendant hardware components to provide such features and functionality.

As shown in FIG. 1, system 100 includes a data processing apparatus 101 that is communicatively coupled to plural emission data sources (e.g., vehicles with onboard emission data collection assemblies) 200-1, 200-2, . . . , 200-m and plural air quality data sources (e.g., sensing stations with ambient air quality data collection assemblies) 300-1, 300-2, . . . , 300-n associated with a monitored area 107 via a network 120 and a control device 150. According to an example implementation, emission data from individual vehicles and air quality data from stationary sensing stations are acquired. In one or more example implementations, emission data retrieved from vehicles 200-1 . . . 200-m up to hundreds of thousands (e.g., m~10-1,000,000) and air quality data retrieved from sensing stations 300-1 . . . 300-n in the tens of thousands (e.g., n~10-100,000) are used. As can be appreciated by one of ordinary skill in the art, the arrangement and density of air quality data sources 300-1 . . . 300-n in a given area 107 (number of sensing stations 300-1 . . . 300-n per squared kilometer in area 107) can be adjusted to improve the coverage and/or resolution of the generated air quality information. In example implementations, system 100 can be applicable plural areas 107.

In an example implementation, onboard emission data collection assemblies 200-1 . . . 200-m can be installed to respective vehicles as a condition for operation in area 107 or as a vehicle maintenance tracking feature. Air quality sensing stations (with ambient air quality data collection assemblies) 300-1 . . . 300-n are placed at respective locations in area 107 and can be oriented in any known arrangements for such purposes. According to an example implementation, sensing stations 300-1 . . . 300-n are arranged at regular intervals along traffic routes, roadways, intersections, and the like, to gather air quality information therefrom. In one or more example implementations, sensing stations 300-1 . . . 300-n can be placed at buildings, enclosures, and the like to retrieve air quality information on a particular zone or enclosure within area 107.

As illustrated in FIG. 1, data processing apparatus 101 is a computing apparatus that incorporates a communication interface 105, one or more processor devices 110, and a memory 115. One or more processor(s) 110 can include any suitable processing circuitry capable of controlling operations and functionality of data processing apparatus 101, as well as facilitating communications between various components within data processing apparatus 101. In some implementations, processor(s) 110 can include a central processing unit ("CPU"), a graphic processing unit ("GPU"), one or more microprocessors, a digital signal processor, or any other type of processor, or any combination thereof. In some implementations, the functionality of processor(s) 110 can be performed by one or more hardware logic components including, but not limited to, field-programmable gate arrays ("FPGA"), application specific integrated circuits ("ASICs"), application-specific standard products ("ASSPs"), system-on-chip systems ("SOCs"), and/or complex programmable logic devices ("CPLDs"). Furthermore, each of processor(s) 110 can include its own local memory, which can store program systems, program data, and/or one or more operating systems.

Memory 115 can include one or more types of storage mediums such as any volatile or non-volatile memory, or any removable or non-removable memory implemented in any suitable manner to store data for data processing apparatus 101. For example, information can be stored using computer-readable instructions, data structures, and/or program systems. Various types of storage/memory can include, but are not limited to, hard drives, solid state drives, flash memory, permanent memory (e.g., ROM), electronically erasable programmable read-only memory ("EEPROM"), CD ROM, digital versatile disk ("DVD") or other optical storage medium, magnetic cassettes, magnetic tape, magnetic disk storage or other magnetic storage devices, RAID storage systems, or any other storage type, or any combination thereof. Furthermore, memory 115 can be implemented as computer-readable storage media ("CRSM"), which can be any available physical media accessible by processor(s) 110 to execute one or more instructions stored within memory 115. In some implementations, one or more applications can be run by processor(s) 110 and can be stored in memory 115.

Communication interface 105 can include any circuitry allowing or enabling one or more components of data processing apparatus 101 to communicate with one or more additional devices, servers, and/or systems—for example, one or more of information system 140, control device 150, emission data collection assemblies 200-1 . . . 200-m, and air quality data collection assemblies 300-1 . . . 300-n. As an illustrative example, data recorded by data collection assemblies 200-1 . . . 200-m and 300-1 . . . 300-n can be transmitted over network 120 to data processing apparatus 101 using any number of communications protocols either directly or through control device 150. For example, network(s) 120 can be accessed using Transfer Control Protocol and Internet Protocol ("TCP/IP") (e.g., any of the protocols used in each of the TCP/IP layers), Hypertext Transfer Protocol ("HTTP"), WebRTC, SIP, and wireless application protocol ("WAP"), are some of the various types of protocols that can be used to facilitate communications between data processing apparatus 101 and control device 150. Various additional communication protocols can be used to facilitate communications between data processing apparatus 101 and control device 150, include the following non-exhaustive list, Wi-Fi (e.g., 802.11 protocol), Bluetooth, radio frequency systems (e.g., 900 MHz, 1.4 GHz, and 5.6 GHz communication systems), cellular networks, FTP, RTP, RTSP, SSH, to name a few.

Communications systems for facilitating network 120 can include hardware (e.g., hardware for wired and/or wireless connections) and/or software. In implementations, communications systems can include one or more communications chipsets, such as a GSM chipset, CDMA chipset, LTE chipset, 4G/5G/6G, Wi-Fi chipset, Bluetooth chipset, to name a few, and/or combinations thereof. Wired connections can be adapted for use with cable, plain old telephone service (POTS) (telephone), fiber (such as Hybrid Fiber Coaxial), xDSL, to name a few, and wired connections can use coaxial cable, fiber, copper wire (such as twisted pair copper wire), and/or combinations thereof, to name a few. Wired connections can be provided through telephone ports, Ethernet ports, USB ports, and/or other data ports, such as Apple 30-pin connector ports or Apple Lightning connector ports, to name a few. Wireless connections can include cellular or cellular data connections and protocols (e.g., digital cellular, PCS, CDPD, GPRS, EDGE, CDMA2000, 1xRTT, RFC 1149, Ev-DO, HSPA, UMTS, 3G, 4G, LTE, 5G, and/or 6G to name a few), Bluetooth, Bluetooth Low Energy, Wi-Fi, radio, satellite, infrared connections, ZigBee communication protocols, to name a few. Communications interface hardware and/or software, which can be used to communicate over wired and/or wireless connections, can include Ethernet interfaces (e.g., supporting a TCP/IP stack), X.25 interfaces, T1 interfaces, and/or antennas, to name a few. Computer systems—such as data processing apparatus 101, information system 140, and control device 150—can communicate with other computer systems or devices directly and/or indirectly, e.g., through a data network, such as the Internet, a telephone network, a mobile broadband network (such as a cellular data network), a mesh network, Wi-Fi, WAP, LAN, and/or WAN, to name a few.

Information system 140 incorporates data storage 145 that embodies storage media for storing data from emission data collection assemblies 200-1 . . . 200-$m$ (which can include operation history, maintenance history, real time location information as well as emission information for each respective vehicle), ambient air quality data collection assemblies 300-1 . . . 300$n$ (including gas composition and particulate matter measure data), data processing apparatus 101 (including results of example data processing described in further detail below), and control device 150 (including operation history, control parameters, location information, etc., related to data collection assemblies 200-1 . . . 200-$m$ and 300-1 . . . 300$n$). Example storage media for data storage 145 correspond to those described above with respect to memory 115. In example implementations, information system 140 incorporates one or more database servers that support Oracle SQL, NoSQL, NewSQL, PostgreSQL, MySQL, Microsoft SQL Server, Sybase ASE, SAP HANA, DB2, and the like. Information system 140 incorporates a communication interface (not shown) for communications with the aforementioned entities—i.e., emission data collection assemblies 200-1 . . . 200-$m$, ambient air quality data collection assemblies 300-1 . . . 300-$n$, data processing apparatus 101, and control device 150—and example implementations of which can include those described above with respect to communication interface 105.

In correspondence with data processing apparatus 101, control device 150 is a computing device with one or more processor(s) 155 example implementations of which can include those described above with respect to processor(s) 110.

Memory 165 can include one or more types of storage mediums such as any volatile or non-volatile memory, or any removable or non-removable memory implemented in any suitable manner to store data for control device 150. Example implementations of memory 165 can include those described above with respect to memory 115.

Communication interface 170 can include any circuitry allowing or enabling one or more components of control device 150 to communicate with one or more additional devices, servers, and/or systems. Example implementations of communication interface 170 can include those described above with respect to communication interface 105. Additionally, communications interface 170 can use any communications protocol, such as any of the previously mentioned example communications protocols for communicating with and controlling emission data collection assemblies 200-1 . . . 200-$m$, ambient air quality data collection assemblies 300-1 . . . 300-$n$, data processing apparatus 101, and information system 140. In some implementations, control device 150 can include one or more antennas to facilitate wireless communications with a network using various wireless technologies (e.g., Wi-Fi, Bluetooth, radiofrequency, etc.). In yet another implementation, control device 150 can include one or more universal serial bus ("USB") ports, one or more Ethernet or broadband ports, and/or any other type of hardwire access port so that communication interface 170 allows control device 150 to communicate with emission data collection assemblies 200-1 . . . 200-$m$, ambient air quality data collection assemblies 300-1 . . . 300-$n$, data processing apparatus 101, information system 140, or another control device (not shown)—for example, via network 120.

User interface 160 is operatively connected to processor(s) 155 and can include one or more input or output device(s), such as switch(es), button(s), key(s), a touch screen, a display, microphone, camera(s), sensor(s), etc. as would be understood in the art of electronic computing devices. Display of user interface 160 can be used to display the results of example processing described in further detail below.

In some implementations, functionality of apparatuses 101 and 150 can be consolidated to a singular apparatus or system that is communicatively coupled to data collection assemblies (200) and (300) for collecting data therefrom and for processing and storing the data in information system 140. In some implementations, information system 140 can also be consolidated with apparatus 101 and/or control device 150. Additionally, in some implementations, separate and independent control devices (not shown) can be incorporated to communicate with and/or control emission data collection assemblies 200-1 . . . 200-$m$ and ambient air quality data collection assemblies 300-1 . . . 300-$n$, respectively. In other words, computing devices and/or data processing apparatuses capable of embodying the systems and/or methods described herein can include any suitable type of electronic device including, but are not limited to, workstations, servers, desktop computers, mobile computers (e.g., laptops, ultrabooks), mobile phones, portable computing devices, such as smart phones, tablets, personal display devices, personal digital assistants ("PDAs"), virtual reality devices, wearable devices (e.g., watches), to name a few. As can be appreciated by one of ordinary skill in the art, the features and functions described herein of control device 150, emission data collection assemblies 200-1 . . . 200-$m$, and ambient air quality data collection assemblies 300-1 . . . 300-*n* can be performed interchangeably among these entities without departing from the spirit and scope of the present disclosure.

Figure 2:
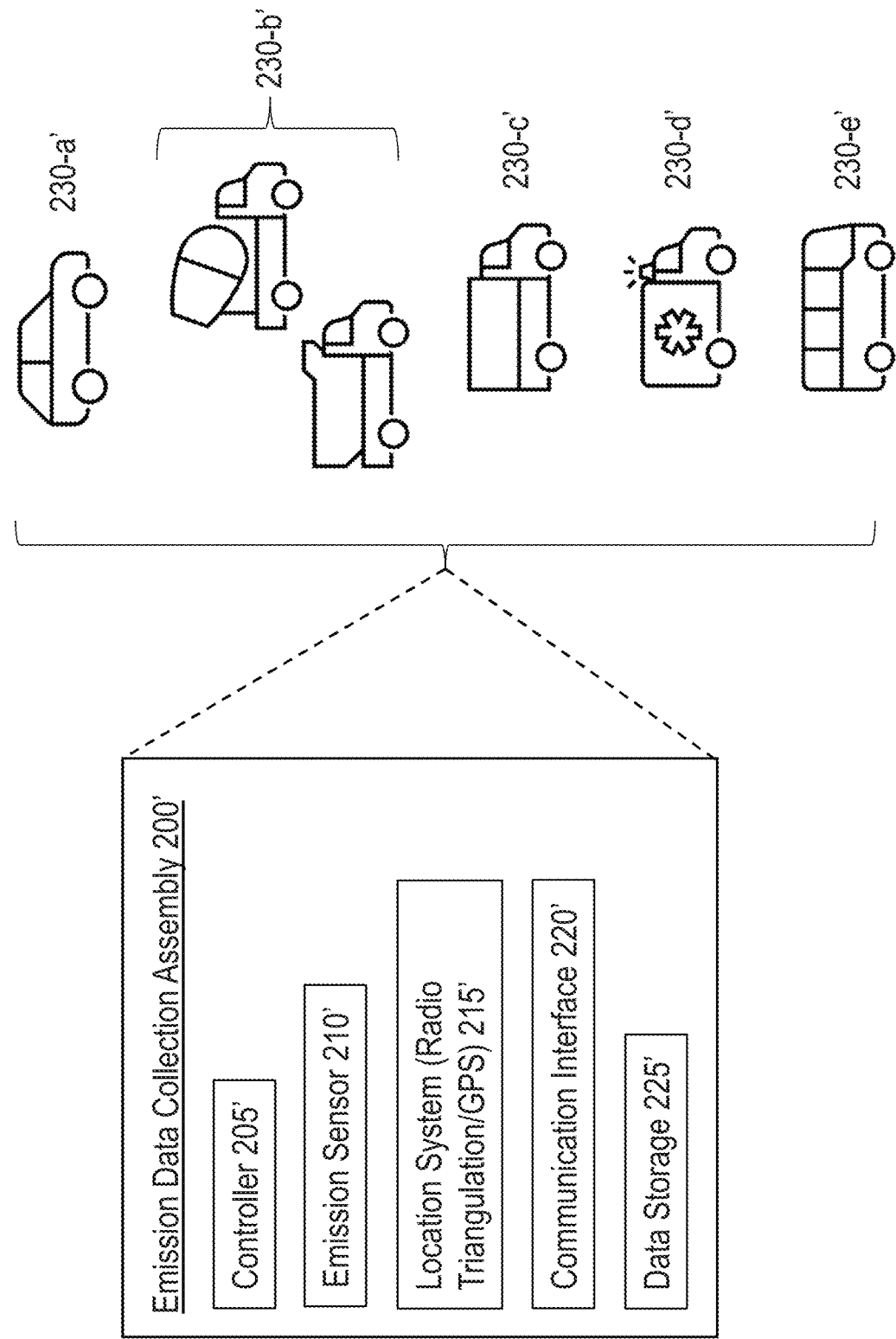
FIG. 2 is a schematic illustration of an emission data collection assembly that is representative of the emission data collection assemblies shown in FIG. 1 according to an example implementation of the present disclosure.

FIG. 2 is a schematic illustration of an emission data collection assembly 200' that is representative of emission data collection assemblies 200-1 . . . 200-*m* shown in FIG. 1 according to an example implementation of the present disclosure. As illustrated in FIG. 2, emission data collection assemblies 200' can be incorporated to, without limitation, regular automobiles (such as family automobiles, taxis, corporate automobiles, limousines, and the like) 230-*a'*, work and construction vehicles 230-*b'*, cargo transportation vehicles (including, for example, fuel delivery vehicles, mail and parcel delivery vehicles, and the like) 230-*c'*, government vehicles (including, for example, police vehicles, fire department vehicles, ambulances to name a few) 230-*d'*, and public transportation vehicles (such as buses, trains, helicopters, airplanes to name a few) 230-*e'* (the different types of vehicles can be collectively referred to herein as 230'). Thus, the emission detection and mitigation management of the present disclosure is applicable, for example, to specific organizations, such as for fleet management of a delivery operation, and to public administration of an area (107), such as a city.

As further illustrated in FIG. 2, each emission data collection assembly 200' incorporates a controller 205', emission sensor 210', location system 215', communication interface 220', and data storage 225'.

Controller 205' incorporates one or more processors (not shown) adapted to control the operations and functionality of emission data collection assembly 200'. Example implementations of controller 205' can include those described above with respect to processor(s) 110.

Emission sensor 210' is a composition sensor, such as an electronic carbon monoxide (CO) sensor, oxygen ($O_2$) sensor, sulfur dioxide ($SO_2$) sensor, nitrogen oxides ($NO_x$) sensor, and the like, that is mounted to the exhaust systems (not shown) of vehicles 230' to determine the emission compositions of the vehicles 230'. As can be appreciated by one of ordinary skill in the art, emission sensor 210' can also embody sensor(s) for detecting particulate matter concentrations from the exhaust systems of vehicles 230'. Thus, according to an example implementation, the collected emission data is used to determine the contributions of the respective vehicles 230' to CO (in parts per million, or ppm) and/or particulate matter pollution in association with data collected by ambient air quality data collection assemblies 300'. Based on data processing discussed below and fuel composition determinations, the collected emission data can also be used to determine contributions to ozone, sulfur dioxide, nitrogen dioxide, and/or lead concentrations according to some implementations of the present disclosure.

Location system 215' includes a sensor adapted to determine the real time locations of vehicles 230'. In example implementations, location system 215' is embodied by one or more of a global position system (GPS) and a radio triangulation location system, which can be integrated with an onboard system (not shown) of the vehicle (230'). In some implementations, location system 215' can include one or more cameras (not shown) that correspond to a navigation system (such as a self-driving system) of the vehicle (230') for improved location determination.

Communication interface 220' can include any circuitry allowing or enabling one or more components of emission data collection assembly 200' to communicate with one or more additional devices, servers, and/or systems. Example implementations of communication interface 220' can include those described above with respect to communication interface 170. Accordingly, communications interface 220' can use any communications protocol, such as any of the previously mentioned example communications protocols for communicating with control device 150, ambient air quality data collection assemblies 300-1 . . . 300-*n*, data processing apparatus 101, and information system 140—for example, via network 120.

Data storage 225' can include one or more types of storage mediums such as any volatile or non-volatile memory, or any removable or non-removable memory implemented in any suitable manner to store data, including any collected emission data and associated location data, for emission data collection assembly 200'. Example implementations of data storage 225' can include those described above with respect to memory 115. In an example implementation, data storage 225' includes a buffer for storing collected real time emission and location data for transmission to control device 150, data processing apparatus 101, and/or information system 140.

In some implementations, emission data collection assembly 200' can be integrated with an onboard system (not shown) of its corresponding vehicle (230'), which can embody control device 150 shown in FIG. 1. As an example, a user interface (such as a console panel and the like) on the vehicle (230') (not shown) can be communicatively coupled to controller 205' for providing user input controls and/or display outputs to an operator of the vehicle (230'). In some implementations, controller 205' can be communicatively coupled to an ignition or starter mechanism, a fuel supply mechanism, or the like, of the vehicle (230') (not shown) so that noncompliance with emission standards results in an inability to operate the vehicle (230'). As an example, a process of setting a time and/or distance limit from an initial determination of emission standard noncompliance can be stored at data storage 225' and executed by controller 205' so that the operator of the vehicle (230') is provided with an opportunity to mitigate the emission noncompliance before the vehicle (230') is rendered inoperable.

Figure 3:
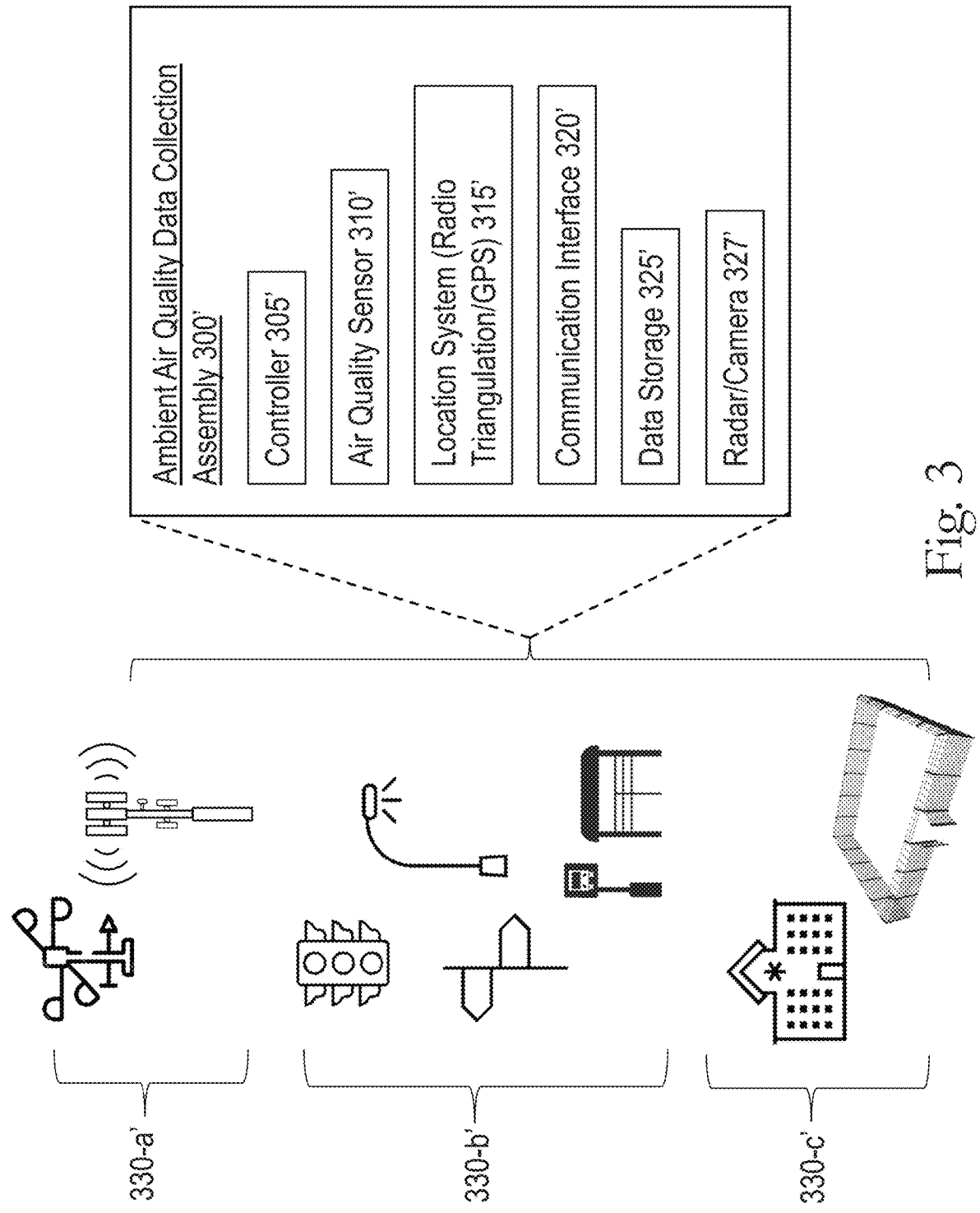
FIG. 3 is a schematic illustration of an ambient air quality data collection assembly that is representative of the emission data collection assemblies shown in FIG. 1 according to an example implementation of the present disclosure.

FIG. 3 is a schematic illustration of an ambient air quality data collection assembly 300' that is representative of emission data collection assemblies 300-1 . . . 300-*n* shown in FIG. 1 according to an example implementation of the present disclosure. As illustrated in FIG. 3, ambient air quality data collection assemblies 300' can be incorporated to, without limitation, structures that are installed at regular intervals throughout an area (107) (such as weather stations and radio communication towers, and the like) 330-*a'*, structures related to roadways and routes (such as traffic lights, street lamps, road signs and markers, bus stops to name a few) 330-*b'*, and buildings and structures associated with an implementation of the present disclosure (such as a hospital, a work site, a transportation hub including a train station and/or an airport, to name a few) 330-*c'* (the different types of structures can be collectively referred to herein as 330'). Thus, as noted above, the ambient air quality detection and associated emission detection and mitigation management of the present disclosure is applicable, for example, to specific organizations, such as for fleet management of a delivery operation, and to public administration of an area (107), such as a city.

As further illustrated in FIG. 3, each ambient air quality data collection assembly 300' incorporates a controller 305', air quality sensor 310', location system 315', communication interface 320', and data storage 325'. In an example implementation, each assembly 300' incorporates a radar and/or camera 327' that is adapted to identify and locate specific vehicles (230') that are noncompliant with respect to emission standards.

Controller 305' incorporates one or more processors (not shown) adapted to control the operations and functionality of ambient air quality data collection assembly 300'. Example implementations of controller 305' can include those described above with respect to processor(s) 110. According to an example implementation, controller 305' can be communicatively coupled to (via communication interface 320'), or integrated with, a control mechanism for a traffic light system (330-b') for altering a traffic direction pattern based on a determination on the detected air quality and contributions from vehicles (230') on the road. According to another example, controller 305' can be communicatively coupled to, or integrated with, bus stop display (330-b') for showing alterations to assigned routes based on a determination on the detected air quality and contributions from vehicles (230') on the road.

Air quality sensor 310' includes a particulate matter sensor and/or a composition sensor, such as an electronic carbon monoxide (CO) sensor, sulfur dioxide ($SO_2$) sensor, nitrogen oxides sensor ($NO_x$) and the like, that is mounted to structures 330' to determine the particulate matter concentration and/or the ambient air composition at and around the locations of the respective structures 330'. In an example implementation, air quality sensor 310' measures and provides an air quality index (AQI), which can indicate air quality of a location in association with multiple pollutants. For example, the AQI can include an indicator for a concentration, in micrograms per meters cubed ($\mu g/m^3$), of PM2.5, which refers to atmospheric particulate matter (PM) that have a diameter of less than 2.5 micrometers. Other measures such as concentrations of ground-level ozone, sulfur dioxide, CO, and nitrogen dioxide (in ppm), and/or lead and particulates such as PM10 (PM having a diameter of less than 10 micrometers) (in $\mu g/m^3$) and the like, can also be included. As can be appreciated by one of ordinary skill in the art, the ambient air quality data collected by assemblies 300' is used to determine the contributions of particular vehicles 230' to particulate matter and/or gaseous pollution in association with data collected by emission data collection assemblies 200'.

Location system 315' includes a sensor adapted to determine the locations of structures 330'. In example implementations, location system 315' is embodied by one or more of a global position system (GPS) and a radio triangulation location system. In some implementations, for example for structures 330' that are radio communication towers (330-a'), location system 315' can cooperate with location systems 215' on the vehicles 230' to determine relative positions and, thus, real time positions of the vehicles 230'. In an example implementation, with structures 330' being fixed to their respective locations, location information is stored in data storage 325', control device 150, data processing apparatus 101, and/or information system 140.

Communication interface 320' can include any circuitry allowing or enabling one or more components of ambient air quality data collection assembly 300' to communicate with one or more additional devices, servers, and/or systems. Example implementations of communication interface 320' can include those described above with respect to communication interface 170. Accordingly, communications interface 320' can use any communications protocol, such as any of the previously mentioned example communications protocols for communicating with control device 150, emission data collection assemblies 200-1 . . . 200-m, data processing apparatus 101, and information system 140—for example, via network 120.

Data storage 325' can include one or more types of storage mediums such as any volatile or non-volatile memory, or any removable or non-removable memory implemented in any suitable manner to store data, including any collected ambient air quality data, for ambient air quality data collection assembly 300'. Example implementations of data storage 325' can include those described above with respect to memory 115. In an example implementation, data storage 325' includes a buffer for storing collected real time air quality data and identified vehicle data (for example, noncompliant vehicles 230' captured by camera 327') for transmission to control device 150, data processing apparatus 101, and/or information system 140.

In some implementations, radar/camera 327' can be integrated with existing traffic control systems, such as traffic violation radar and camera systems (not shown) and the like. Accordingly, based on vehicle emission plume air dispersion modelling and collected air quality measures, real time pollution contributions of respective vehicles 230' can be determined and noncompliant vehicles can be identified. According to an example implementation, in a manner similar to a traffic violation radar and camera system, radar/camera 327' captures an image of a noncompliant vehicle 230' based upon which the identification of the vehicle 230' can be used to undertake remedial and/or punitive actions, such as a citation and/or a fine.

In some implementations, ambient air quality data collection assemblies 300' can be deployed on a mobile vehicle, such as vehicles 230', to determine ambient air quality at different locations at different times in area 107, which is recorded and which is identifiable to the time and location at which the air quality data is recorded. The data can be stored over predetermined periods at control device 150, data processing apparatus 101, and/or information system 140 for processing and interpretation.

Figure 4:
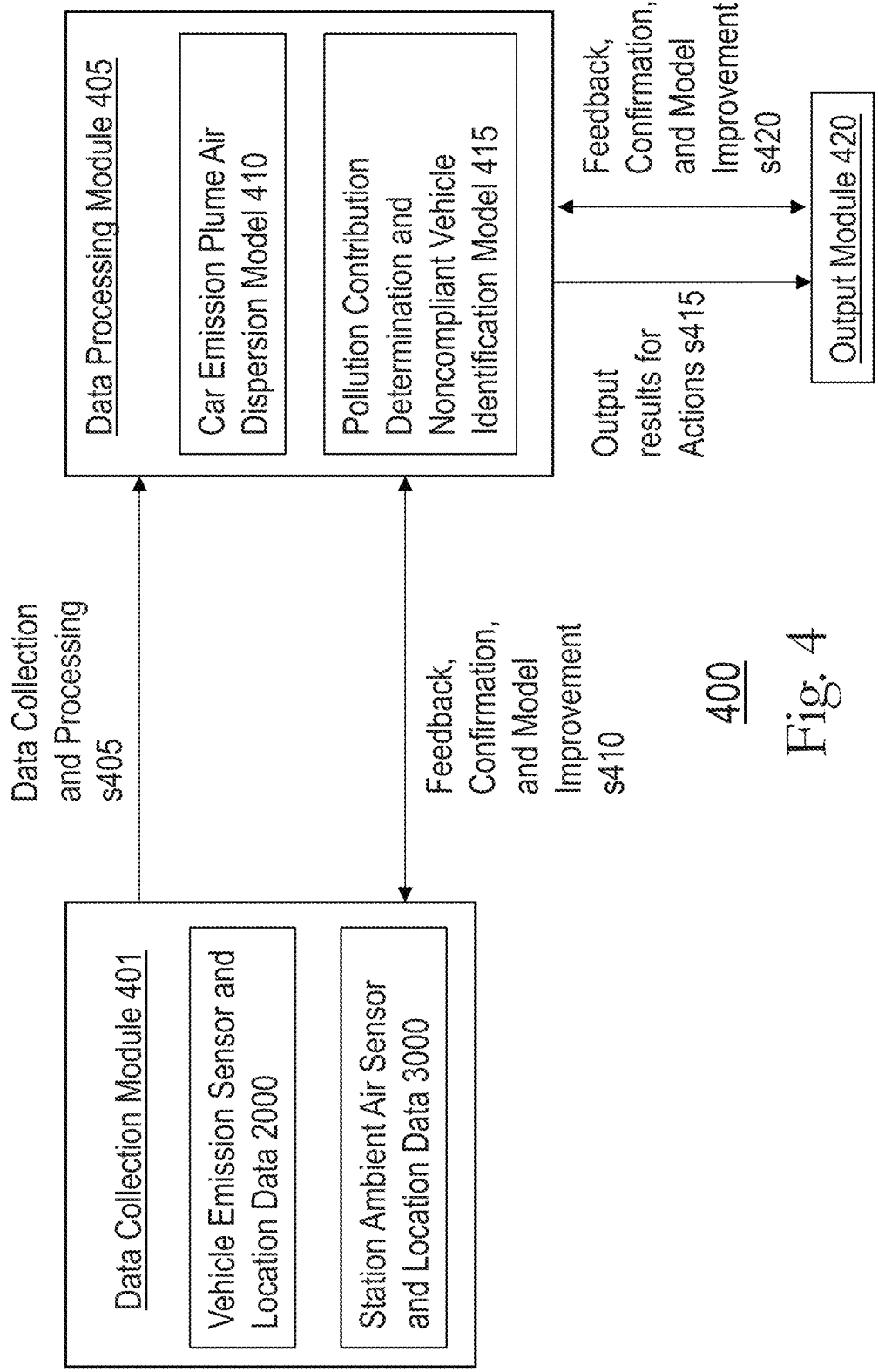
FIG. 4 is a schematic illustration of a software structure maintained at one or more of a data processing apparatus, an information system, a control device, one or more emission data collection assemblies, and one or more ambient air quality data collection assemblies in accordance with an example implementation of the present disclosure.

FIG. 4 is a schematic illustration of a software structure 400 maintained at one or more of data processing apparatus 101, information system 140, control device 150, emission data collection assemblies 200', and ambient air quality data collection assemblies 300' in accordance with an example implementation of the present disclosure. FIG. 4 further illustrates steps conducted by these modules in an example implementation of the present disclosure.

As shown in FIG. 4, software structure 400 includes a data collection module 401, a data processing module 405, and an output module 420. Data collection module 401 includes instructions for collecting vehicle emission sensor and location data 2000, which corresponds to data collected by emission data collection assemblies 200' described above. Data collection module 401 further includes instructions for collecting station ambient air sensor and location data 3000, which corresponds to data collected by ambient air quality collection assemblies 300' described above. Thus, data collection module 401, in an initial step s405, outputs the collected data 2000 and 3000 to data processing module 405.

Data processing module 405 includes instructions for incorporating vehicle emission plume air dispersion model 410 to process the collected vehicle emission sensor and location data 2000 and station ambient air sensor and location data 3000. According to an example implementation, vehicle emission plume air dispersion model 410 includes one or more of, without limitation, Gaussian dispersion models, convective scaling, plume rise and dispersion models, Lagrangian dispersion models and equations, and the like. In example implementations, an AMS/EPA (American Meteorological Society/United States Environmental Protection Agency) Regulatory Model (AERMOD) atmospheric dispersion modeling system and/or a "California Puff Model" (CALPUFF) air quality dispersion modeling system can be incorporated in developing small scale dispersion modeling on individual vehicles, emission elements, and the like. Based on model 410, data processing module 405 employs a pollution contribution determination and noncompliant vehicle identification model 415 to process the collected data 2000 and 3000 and determine the respective contributions of vehicles 230' to ambient pollution around structures 330' in area 107. Based on these determinations, noncompliant vehicles are identified. According to an example implementation, a noncompliant vehicle can be one of the vehicles 230' incorporated with an emission data collection assembly 200' or can be a vehicle without emission data collection assembly 200'.

In a step s410, data processing module 405 processes the output from one or more of vehicle emission plume air dispersion model 410 and pollution contribution determination and noncompliant vehicle identification model 415 with collection data 2000 and 3000, which can include additional collected data such as images captured by camera 327', updated air quality data based on changed conditions from output results of output module 420, and the like, for feedback and confirmation of the processing results. Based on any feedback adjustments and confirmations of the processing results at step s410, models 410 and 415 are updated and improved. In some implementations, one or more machine learning based models can be used for models 410, 415 and step s410.

Next, in a step s415, data processing module 405 outputs confirmed processing results to output module 420 for intervention, punitive, or remedial actions. As discussed above, output module 420 can issue an instruction to a controller 205' of a noncompliant vehicle 230' to set a time and/or distance limit before rendering vehicle 230' inoperable. Correspondingly, an alert can be issued to the operator of the noncompliant vehicle 230'—for example, via a display (not shown) at the vehicle 230'—to perform maintenance services on the noncompliant vehicle 230'. As another example, output module 420 can issue an instruction for generating a citation ticket for the noncompliant vehicle 230'. As yet another example, output module 420 can issue instructions to public transportation vehicles (230-e') to alter their assigned routes based on traffic emission conditions. Correspondingly, instructions to transportation routing displays, such as bus stops (330-b'), can be issued to show the alterations to the assigned routes. For fleet management applications, output module 420 can issue an instruction to a vehicle maintenance administration apparatus (not shown) to schedule maintenance services to respective vehicles 230' in a fleet based on outputs at step s415.

Finally, at step s420, output module 420 returns feedback and confirmations to data processing module 405 to further improve model 410 and/or model 415. In example implementations, the feedback at step s420 can include, without limitation, citation disputes and associated evidence, operator or administrator feedback via message communications, vehicle inspection results to name a few. Confirmations at step s420 can include, for example, a collected fine, a vehicle service record (of maintenance services performed following the processing results of step s415) to name a few.

Example 1

Figure 5:
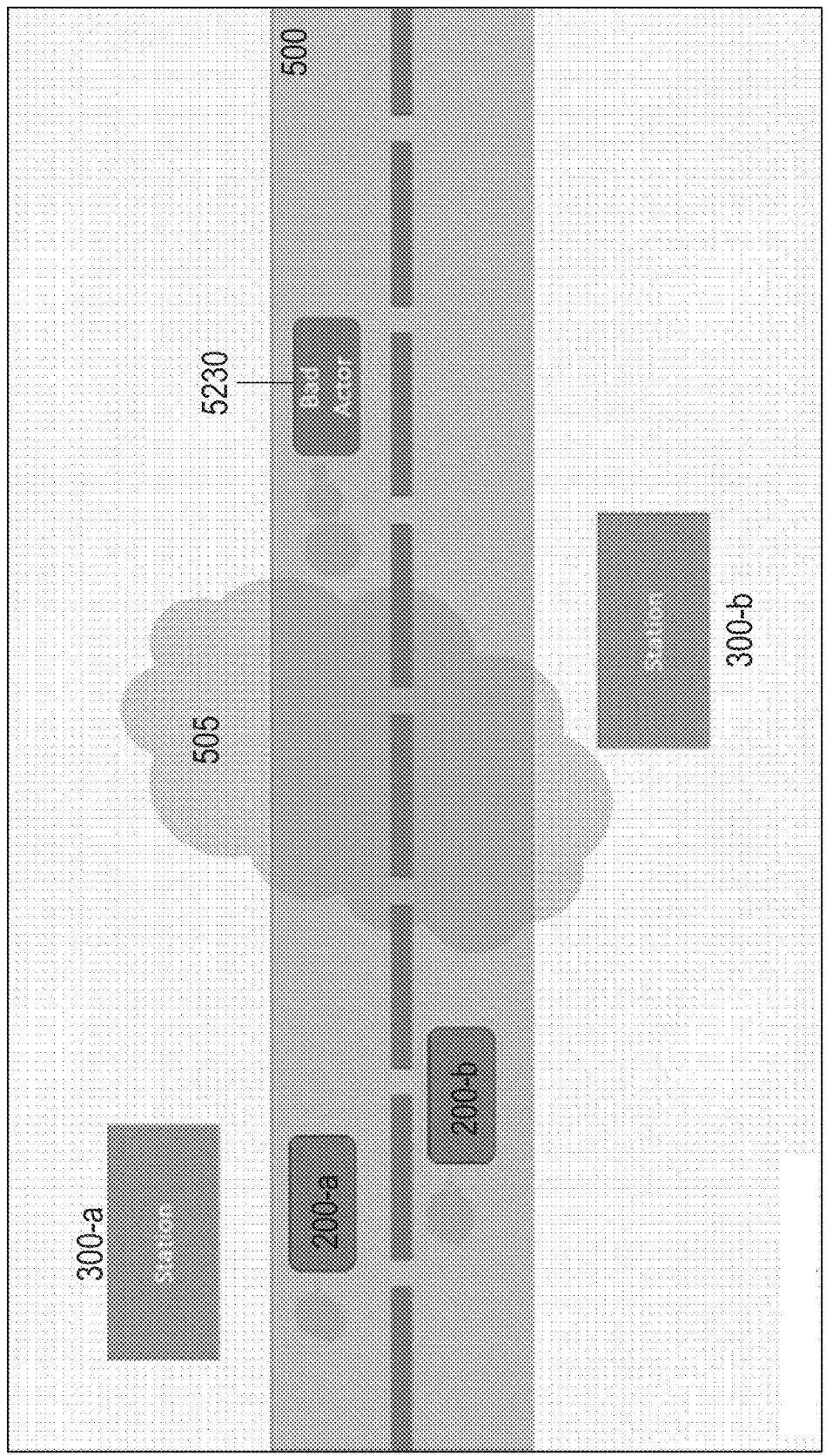
FIG. 5 is a graphical illustration of an example implementation of the present disclosure.

FIG. 5 is a graphical illustration of an example implementation of the present disclosure. As shown in FIG. 5, a roadway section 500, which can be situated in area 107 shown in FIG. 1, includes two ambient air quality data collection assemblies 300-a and 300-b mounted at respective "stations," which can be roadside structures that are placed at regular intervals along the roadway of section 500. As further illustrated in FIG. 5, two vehicles with respective onboard emission data collection assemblies 200-a and 200-b are operating on the roadway section 500.

According to an example implementation, a pollutant emission plume 505 from a "bad actor" noncompliant vehicle 5230 causes assemblies 300-a and 300-b in its vicinity to detect elevated levels of pollution (e.g., airborne pollutants and concentrations). Based on vehicle emission plume air dispersion model 410 and collected emission and location data from assemblies 200-a and 200-b (which are in the vicinity of vehicle 5230), data processing module 405 executing model 415 can determine that the source of pollutant emission plume 505 is from neither vehicle associated with assemblies 200-a and 200-b, respectively. Radar/camera 327' of one or more of assemblies 300-a and 300-b can determine the presence and position of noncompliant vehicle 5230. Based on the position of vehicle 5230, models 410 and 415, and data from assemblies 200-a, 200-b, 300-a, and 300-b, an image can be taken of vehicle 5230 to identify it as a principal source of plume 505. Accordingly, the image can form a basis for issuing a citation to the operator of vehicle 5230.

In an example implementation, data from an onboard emission data collection assembly 200' at vehicle 5230 can provide further improvements to models 410 and 415—for example, at step s410. As discussed above, vehicle 5230 incorporating an onboard emission data collection assembly 200' can receive an alert for display to the operator of vehicle 5230 and/or an instruction for rendering vehicle 5230 inoperable (via a control to a starter or fuel supply mechanism on vehicle 5230) within a time or distance limit from the above-described identification of vehicle 5230 as the principal source of plume 505.

In other words, the present disclosure provides for identifying noncompliant vehicle 5230 both when vehicle 5230 incorporates an emission data collection assembly 200' and when it does not.

Example 2

According to an example implementation, the air quality data from assemblies 300' augmented with emission information from assemblies 200 outputted by data processing apparatus 101 is used to adjust, alter, and enhance traffic direction operations via traffic lights, such as element 300-2 shown in FIG. 1, or digital road signs (330-b'), which can be controlled via control device 150. Based on detected pollution (e.g., airborne pollutant concentrations) on particular roadways, traffic on these roadways can be prioritized (e.g., with altered "stop" and "go" durations) or diverted (e.g., by altering directions on road signs) to reduce the risk of sustained elevated pollution (e.g., elevated airborne pollutant concentrations). As an example, a metropolitan area with high population and vehicle densities—and emissions (e.g., Paris)—can implement the methods, apparatuses, and systems of the present disclosure to quickly identify bad actors and/or divert potential sources of pollution away from city centers or high pollution risk areas.

Portions of the methods described herein can be performed by software or firmware in machine readable form on a tangible (e.g., non-transitory) storage medium. For example, the software or firmware can be in the form of a computer program including computer program code adapted to cause the system to perform various actions described herein when the program is run on a computer or suitable hardware device, and where the computer program can be embodied on a computer readable medium. Examples of tangible storage media include computer storage devices having computer-readable media such as disks, thumb drives, flash memory, and the like, and do not include propagated signals. Propagated signals can be present in a tangible storage media. The software can be suitable for execution on a parallel processor or a serial processor such that various actions described herein can be carried out in any suitable order, or simultaneously.

It is to be further understood that like or similar numerals in the drawings represent like or similar elements through the several figures, and that not all components or steps described and illustrated with reference to the figures are required for all implementations or arrangements.

The terminology used herein is for the purpose of describing particular implementations only and is not intended to be limiting of the invention. As used herein, the singular forms "a," "an," and "the" are intended to include the plural forms as well, unless the context clearly indicates otherwise. It will be further understood that the terms "contains", "containing", "includes", "including," "comprises", and/or "comprising," and variations thereof, when used in this specification, specify the presence of stated features, integers, steps, operations, elements, and/or components, but do not preclude the presence or addition of one or more other features, integers, steps, operations, elements, components, and/or groups thereof.

Terms of orientation are used herein merely for purposes of convention and referencing and are not to be construed as limiting. However, it is recognized these terms could be used with reference to an operator or user. Accordingly, no limitations are implied or to be inferred. In addition, the use of ordinal numbers (e.g., first, second, third) is for distinction and not counting. For example, the use of "third" does not imply there is a corresponding "first" or "second." Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

While the disclosure has described several example implementations, it will be understood by those skilled in the art that various changes can be made, and equivalents can be substituted for elements thereof, without departing from the spirit and scope of the invention. In addition, many modifications will be appreciated by those skilled in the art to adapt a particular instrument, situation, or material to implementations of the disclosure without departing from the essential scope thereof. Therefore, it is intended that the invention not be limited to the particular implementations disclosed, or to the best mode contemplated for carrying out this invention, but that the invention will include all implementations falling within the scope of the appended claims.

The subject matter described above is provided by way of illustration only and should not be construed as limiting. Various modifications and changes can be made to the subject matter described herein without following the example implementations and applications illustrated and described, and without departing from the true spirit and scope of the invention encompassed by the present disclosure, which is defined by the set of recitations in the following claims and by structures and functions or steps which are equivalent to these recitations.

What is claimed is:

1. An apparatus adapted to identify one or more sources of an airborne pollutant in a geographical area and to mitigate release of the airborne pollutant, comprising:
   a processor;
   a communication interface to one or more networks;
   a non-transitory computer-readable memory operatively connected to the processor and having stored thereon machine-readable instructions to:
      receive, via the communication interface from a plurality of emission data collection assemblies, emission data and vehicle location data associated with a plurality of corresponding vehicles in the geographical area;
      receive, via the communication interface from a plurality of ambient air quality collection assemblies at respective locations in the geographical area, ambient air quality data for the respective locations in the geographical area;
      apply a vehicle emission plume air dispersion model to process the received emission data, the received vehicle location data, and the received ambient air quality data;
      identify one or more principal sources of the airborne pollutant based on the processed emission data, vehicle location data, and ambient air quality data; and
      transmit, via the communication interface, an instruction related to one or more vehicles associated with the one or more identified principal sources of the airborne pollutant.

2. The apparatus of claim 1, wherein the instruction comprises one or more of a distance limit and a time limit from a corresponding one or more of a location and a time associated with the identification of one or more principal sources of the airborne pollutant to render inoperable the one or more vehicles.

3. The apparatus of claim 1, wherein the instruction comprises a citation related to each of the one or more vehicles based on the identification of the one or more principal sources of the airborne pollutant.

4. The apparatus of claim 1, wherein the instruction comprises an alert for performing maintenance services on the one or more vehicles based on the identification of the one or more principal sources of the airborne pollutant.

5. The apparatus of claim 1, wherein the identification of the one or more principal sources of the airborne pollutant comprises identifying at least one vehicle without an emission data collection assembly as at least one of the one or more principal sources of the airborne pollutant.

6. The apparatus of claim 5, wherein the at least one vehicle without an emission data collection assembly is identified based on the processed emission data and vehicle location data associated with one or more of the plurality of corresponding vehicles in a vicinity of the identified at least one vehicle.

7. The apparatus of claim 5, wherein the at least one vehicle without an emission data collection assembly is identified based on the processed ambient air quality data for one or more of the respective locations in a vicinity of the identified at least one vehicle.

8. The apparatus of claim 1, wherein the instruction comprises an alteration to an assigned route related to the one or more vehicles associated with the one or more identified principal sources of the airborne pollutant.

9. The apparatus of claim 1, wherein the instruction comprises an alteration to one or more of a traffic light and a road sign related to the one or more vehicles associated with the one or more identified principal sources of the airborne pollutant.

10. A method for identifying one or more sources of an airborne pollutant in a geographical area and for mitigating release of the airborne pollutant, comprising:

receiving, by a processing apparatus via a communication interface from a plurality of emission data collection assemblies, emission data and vehicle location data associated with a plurality of corresponding vehicles in the geographical area;

receiving, by the processing apparatus via the communication interface from a plurality of ambient air quality collection assemblies at respective locations in the geographical area, ambient air quality data for the respective locations in the geographical area;

applying, by the processing apparatus, a vehicle emission plume air dispersion model to process the received emission data, the received vehicle location data, and the received ambient air quality data;

identifying, by the processing apparatus, one or more principal sources of the airborne pollutant based on the processed emission data, vehicle location data, and ambient air quality data; and transmitting, by the processing apparatus via the communication interface, an instruction related to one or more vehicles associated with the one or more identified principal sources of the airborne pollutant.

11. The method of claim 10, wherein the instruction comprises one or more of a distance limit and a time limit from a corresponding one or more of a location and a time associated with the identifying of the one or more principal sources of the airborne pollutant to render inoperable the one or more vehicles.

12. The method of claim 10, wherein the instruction comprises a citation related to each of the one or more vehicles based on the identifying of the one or more principal sources of the airborne pollutant.

13. The method of claim 10, wherein the instruction comprises an alert for performing maintenance services on the one or more vehicles based on the identifying of the one or more principal sources of the airborne pollutant.

14. The method of claim 10, wherein the identifying of the one or more principal sources of the airborne pollutant comprises identifying at least one vehicle without an emission data collection assembly as at least one of the one or more principal sources of the airborne pollutant.

15. The method of claim 14, wherein the at least one vehicle without an emission data collection assembly is identified based on the processed emission data and vehicle location data associated with one or more of the plurality of corresponding vehicles in a vicinity of the identified at least one vehicle.

16. The method of claim 14, wherein the at least one vehicle without an emission data collection assembly is identified based on the processed ambient air quality data for one or more of the respective locations in a vicinity of the identified at least one vehicle.

17. The method of claim 10, wherein the instruction comprises an alteration to an assigned route related to the one or more vehicles associated with the one or more identified principal sources of the airborne pollutant.

18. The method of claim 10, wherein the instruction comprises an alteration to one or more of a traffic light and a road sign related to the one or more vehicles associated with the one or more identified principal sources of the airborne pollutant.

* * * * *